United States Patent [19]

Gabbay et al.

[11] 4,185,636
[45] Jan. 29, 1980

[54] SUTURE ORGANIZER, PROSTHETIC DEVICE HOLDER, AND RELATED SURGICAL PROCEDURES

[75] Inventors: Shlomo Gabbay, Bronx; Robert Frater, Bronxville, both of N.Y.

[73] Assignee: Albert Einstein College of Medicine of Yeshiva University, Bronx, N.Y.

[21] Appl. No.: 865,481

[22] Filed: Dec. 29, 1977

Related U.S. Application Data

[63] Continuation-in-part of Ser. No. 781,538, Mar. 28, 1977, abandoned.

[51] Int. Cl.$^2$ .............................................. A61B 17/04
[52] U.S. Cl. .............................. 128/334 R; 24/81 CC;
 24/115 R; 24/255 R; 24/262; 339/255 R
[58] Field of Search .............. 128/303 R, 334 R, 335,
 128/335.5; 211/60 R, 67, 120; 24/81 CC, 115
 R, 255 R, 262; 339/255 R

[56] References Cited

U.S. PATENT DOCUMENTS

| 2,692,599 | 10/1954 | Creelman | 128/303 R |
| 3,515,129 | 6/1970 | Truhan | 128/20 |

FOREIGN PATENT DOCUMENTS 1360771 7/1974 United Kingdom ................ 128/334 R
388739 10/1973 U.S.S.R. ........................... 128/334 R

*Primary Examiner*—Dalton L. Truluck
*Attorney, Agent, or Firm*—Stephen E. Feldman; Marvin Feldman

[57] ABSTRACT

A plurality of organizers each formed with an arcuate support member upon which a selected number of suture holding devices are positioned in spaced relationship one to the other, are each designed to be disposed proximate an area of a body upon which surgery is to be performed to faciliate speedy and orderly control of interrupted sutures and needles utilized during the surgical procedure. Each holding device includes a pair of spaced wall members and a resilient holding member disposed in compression therebetween in such a manner that sutures can be releasably held between the resilient member and the adjacent wall member surface. Additional valuable time for surgical procedures involving insertion of artificial heart valves can be saved by utilizing a heart valve holder having a plurality of circumferentially spaced legs, to which an artificial heart valve can be releasably held by sutures. The legs which depend from an internally threaded holder formed for co-action with a rod slidably positioned in a holding disk which carries spring clips about its circumferential edge for releasable coaction with the sutures utilized to secure the valve in place.

11 Claims, 12 Drawing Figures

FIG. 4
FIG. 3
FIG. 5
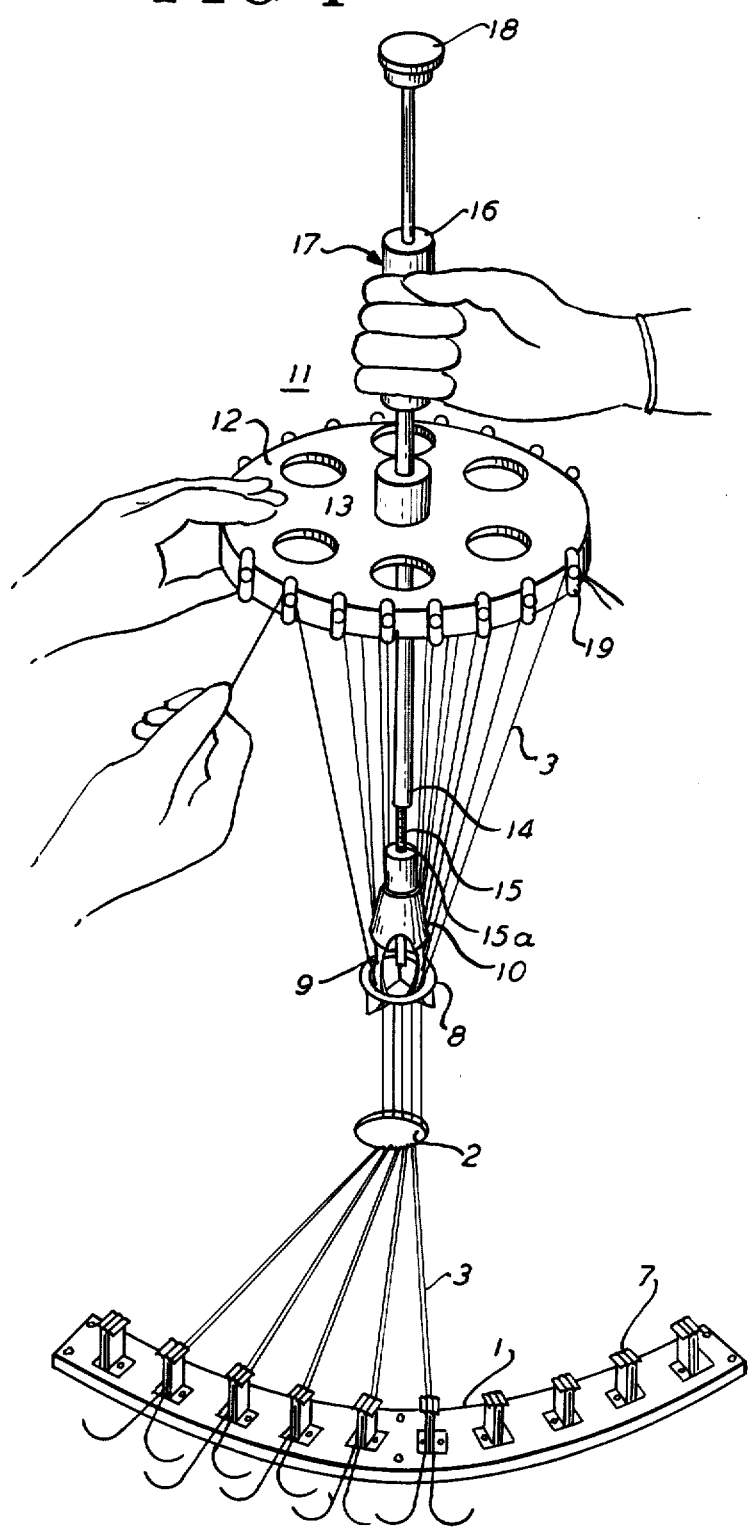
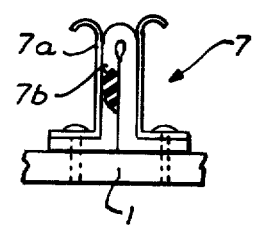
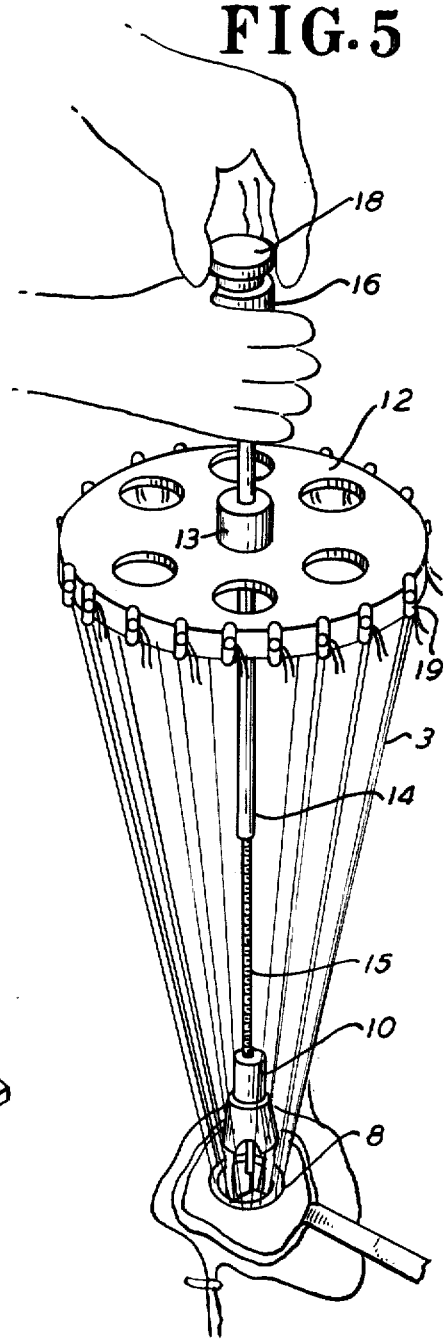

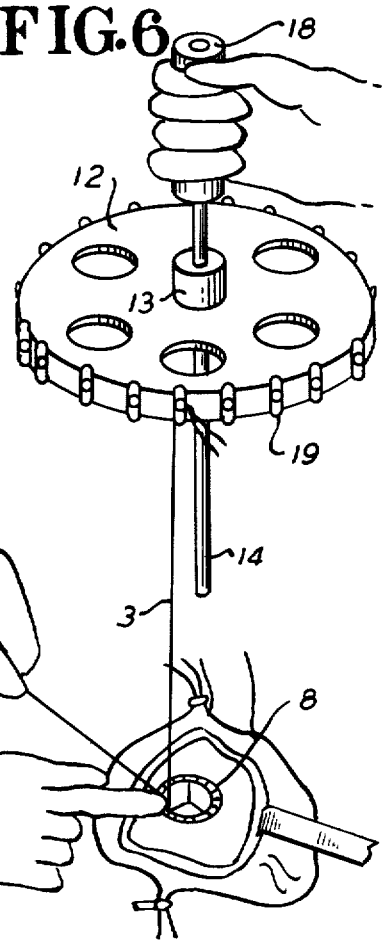
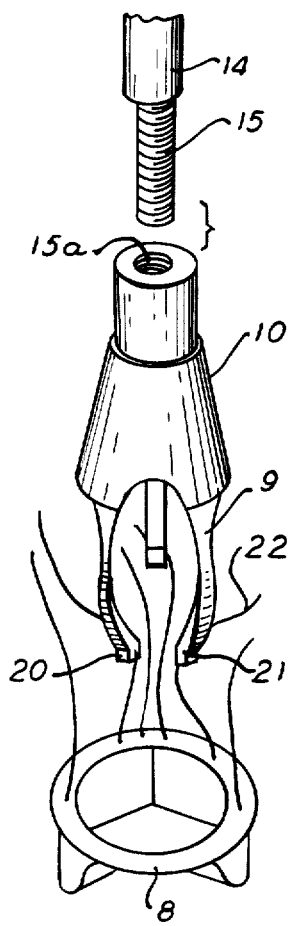
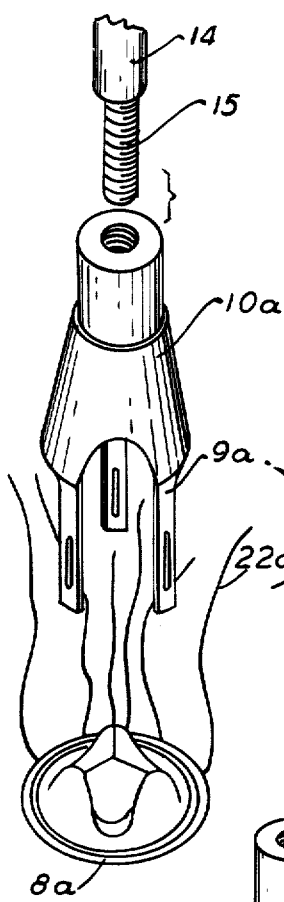
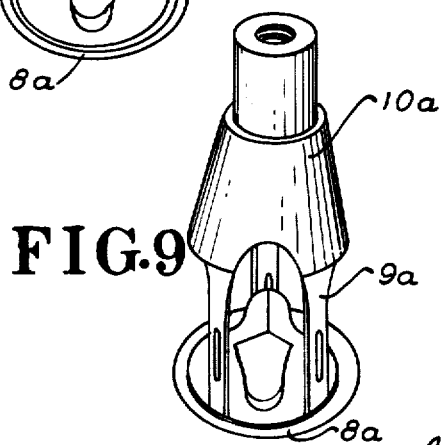
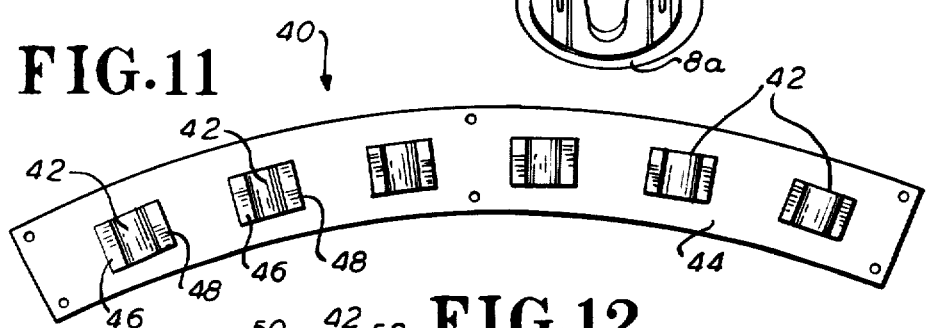
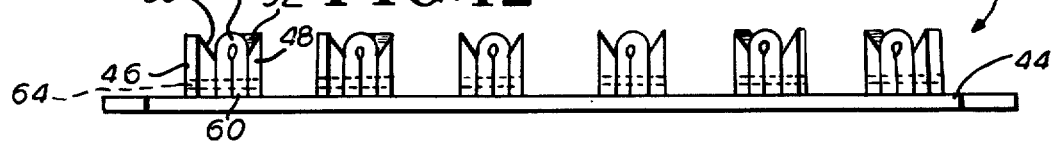

SUTURE ORGANIZER, PROSTHETIC DEVICE HOLDER, AND RELATED SURGICAL PROCEDURES

REFERENCE TO RELATED APPLICATION

This application is a continuation-in-part of application Ser. no. 781,538 filed Mar. 28, 1977, now abandoned.

BACKGROUND OF THE INVENTION—FIELD OF APPLICATION

This invention relates to surgical procedures and devices utilized to facilitate speedy and orderly surgical procedures; and more particularly to holders for sutures and prosthetic devices and related surgical procedures.

BACKGROUND OF THE INVENTION—DESCRIPTION OF THE PRIOR ART

The time consumed in completing a serious medical operation, particularly operations which involve the exposure of the internal body cavity, is of extreme importance to the survival of the patient. Experience has shown that there is a direct relationship between the time span of the operation and its success.

The above factors are particularly true in connection with such serious operations as open-heart surgery where there is not only the problem of exposure but which involves the use of artificial/mechanical means for maintaining the vital functions of the patient during the operation. In such operations, one of the more time-consuming steps involved in replacing a defective heart valve with an artificial valve is the attachment of the valve to the heart by means of multiple sutures, and this, of course, during the time when the patient is relying upon outside artificial means to sustain his or her life. During aortic valve replacement, the heart itself is cut off from the general circulation and is thereby denied the oxygen and nutrients it needs to maintain its integrity as a living tissue. During mitral valve replacement, some perfusion of the heart muscle is maintained, but not at an optimal level. Thus there are compelling advantages to keeping the heart muscle at risk for only the shortest possible time span.

During the type of operation above described, it may be necessary to connect the artificial valve to the natural annulus of the heart valve by twenty or more sutures, all of which will eventually be projecting from the site of the attachment; which is a relatively small space. Consequently, it often becomes very difficult to keep the individual sutures separated, and valuable time may be lost in doing so, and in locating the proper suture pairs which are to be tied and knotted.

It is also imperative to keep count of the needles utilized in sewing the sutures since all such needles must be accounted for before the body cavity is closed. The search for lost needles prolongs the time of the surgery and adds additional risk for the patient.

The proper positioning of the prosthetic device being implanted is also quite essential if the surgical procedure is to be successful. Placement by hand is often difficult if not impossible due to the size of the device to be implanted, the restricted size of the area of implant and the conditions surrounding same. The use of complex holding devices facilitates the space problem, but often increases the time of the operation with attendant concerns.

SUMMARY OF THE INVENTION

It is therefore an object of this invention to provide a new and improved holder for sutures.

It is another object of this invention to provide a new and improved holder for multiple sutures.

It is yet another object of this invention to provide a new and improved holder and organizer for multiple interrupted sutures.

It is yet still another object of this invention to provide a new and improved holder and organizer for multiple interrupted sutures and their associated surgical needles.

It is yet still another object of this invention to provide a new and improved device for holding a prosthetic device during surgical implantation thereof.

It is yet still a further object of this invention to provide a new and improved device for holding an artificial heart valve for surgical implantation thereof.

It is yet still a further object of this invention to provide new and improved surgical procedures for orderly control of multiple interrupted sutures and for implantation of prosthetic devices such as artificial heart valves.

This invention involves surgical procedures requiring the use of multiple interrupted sutures, and especially surgical procedures for anastomoses and implantation of artificial heart valves; and contemplates providing one or more organizers for releasably holding sutures and associated needles in a selected, orderly and controlled arrangement; providing a holder for releasably holding and positioning the prosthetic device for implantation; with related surgical procedures.

In carrying out the invention, according to the preferred embodiments each organizer is formed to carry a plurality of holders each, in turn, formed to releasably accept and readily release either or both ends of an interrupted suture; the prosthetic device holder includes a number of depending arms which resiliently grip the prosthetic device and to which the prosthetic device may be sutured; and the surgical procedures utilize one or more of such organizers and prosthetic device holders.

Other objects, features, and advantages of the invention in its details of construction and arrangement of parts will be seen from the above, from the following description of the preferred embodiment when considered in conjunction with the drawings and from the appended claims.

BRIEF DESCRIPTION OF THE DRAWING

In the drawings:

FIG. 3 is an enlarged view of an individual suture holder;

FIG. 4 illustrates the use of a suture holder as shown in FIG. 1, together with a valve and suture holder device also incorporating the instant invention;

FIGS. 5 and 6 illustrates sequential steps taking place during the implantation and suturing of an artificial valve following the initial step illustrated in FIG. 4;

FIG. 7 illustrates the combination of a mitral valve and valve holder in accordance with this invention;

FIG. 8 illustrates the disconnection between the valve holder and the artificial mitral valve;

FIGS. 9 and 10 are similar to FIGS. 7 and 8, showing an artificial aortic valve;

FIG. 11 is a plan view of a further modified form of suture organizer incorporating the instant invention; and FIG. 12 is an elevational view of the suture organizer of FIG. 11.

DESCRIPTION OF THE PREFERRED EMBODIMENT

Figure 1:
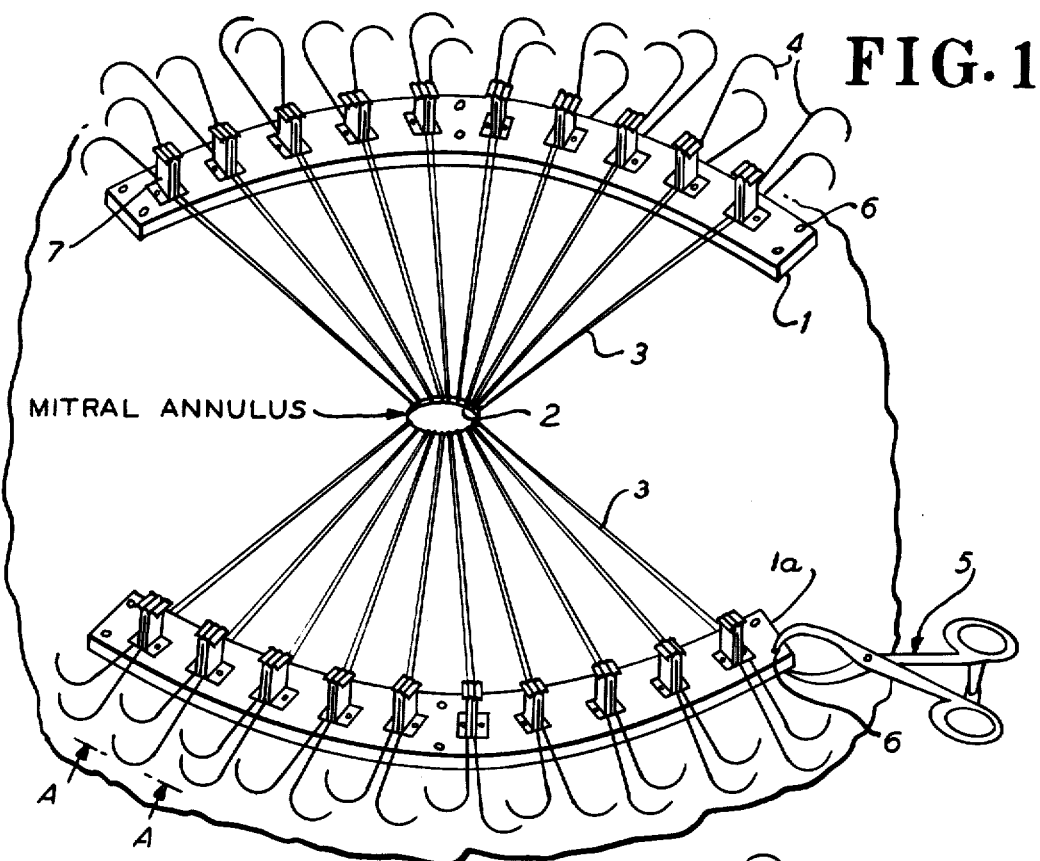
FIG. 1 is a plan view of a pair of suture organizers or retractors, incorporating the instant invention.

According to the invention as shown in FIG. 1, individual suture holders (to be hereinafter described in detail) are maintained by suitable and conventional means upon arcuately shaped supports or organizers 1 and 1a which will be placed upon the body of the patient (not shown) but on substantially opposite sides of the situs of the operation which in this case may be the mitral annulus 2. Multiple sutures 3 are threaded about the circumference of the annulus and for this purpose are preferably provided with needles 4. Except for the space immediately surrounding the situs of the operation, the body of the patient is generally covered with toweling or other suitable material and the frames 1 and 1a are sufficiently held in place by clamping to these towels through the use of a clamp 5 which may engage the frames through the use of openings 6. While frames 1 and 1a are shown as arcuate, other suitable configurations may be used.

Figure 2:
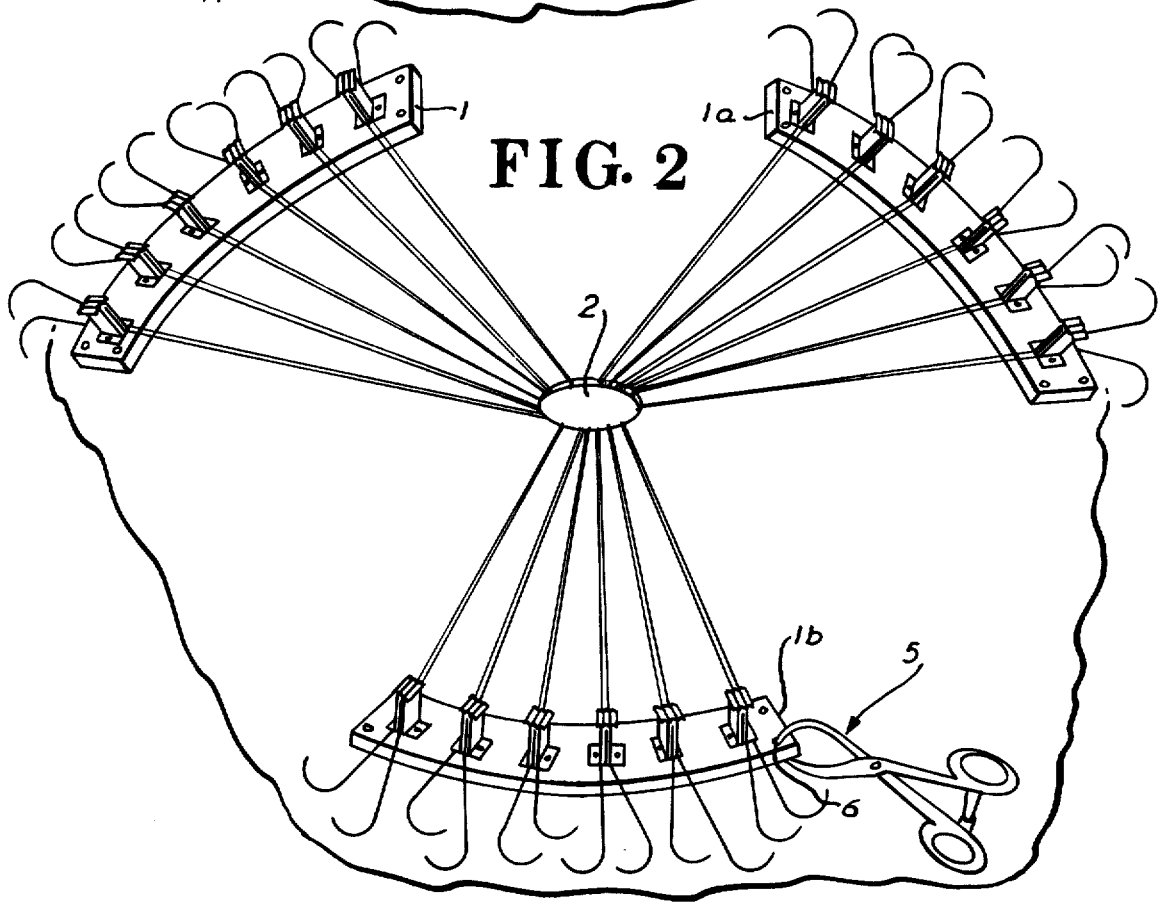
FIG. 2 is a plan view illustrating a modified form and arrangement of suture organizers.

Instead of utilizing two organizers, as illustrated in FIG. 1, it may for certain purposes be more convenient to utilize three or more such organizers as illustrated in FIG. 2, at 1, 1a and 1b.

The construction of the individual suture holders 7 (FIG. 3) is of extreme importance in that they must firmly engage the sutures against lateral motion but must also permit the individual sutures to be quickly disengaged as by an upward motion therefrom. To that end, each individual suture holder is formed by a pair of spaced, preferably stainless steel or plastic, spring arms 7A between which is compressed a piece of soft rubber bent back upon itself, indicated at 7B. The combination of steel and soft rubber making up each individual suture holder is attached to frame 1 by suitable means such as bolts or rivets frame 1.

FIG. 4, illustrates an assisting device for use in the attachment of an artificial valve 8 to the annulus 2 of a diseased heart valve, and, as is shown, it is assumed that the diseased natural valve has already been removed; the patient at this point being maintained by artificial means such as an external heart-lung machine. The basic sutures 3 are now in place and are being held by the individual suture holders 7 mounted on frame 1. The mitral valve 8, to be attached to the annulus 2, is temporarily attached by sutures 3 to the arms 9 extending from a disposable plastic valve holder 10. Holder 10 may be made from plexiglass or other suitable material, and it is contemplated that valve holder 10 and the valve 8 may be a preconnected unit individually packaged and supplied to the surgeon. The combination of valve 8 and valve holder 10 is illustrated in more detail in FIGS. 7-10 and will be described in more detail hereinafter.

The application and attachment of artificial valve 8, to the annulus 2 of the diseased valve is preferably effected through an assisting device generally indicated at 11 in FIG. 4, consisting first of a plastic disk 12 provided with an integral hub 13 through which may be slidably moved, a rod 14 preferably of stainless steel and provided with an externally threaded projection 15 engaging an internally threaded opening 15a in the top of disposable valve holder 10. Spaced above and integral with hub 13 is a hand grip 16 having a threaded opening into which a set screw 17 is threaded. The upper end of rod 14 is provided with a knob 18.

A plurality of spring clips 19 are attached about the outer periphery of the disk 12 for holding sutures 3 in a manner hereinafter described.

Disposable valve holder 10 and its attached mitral valve 8 are illustrated in more detail in FIGS. 7 and 8, from which it will be seen that legs 9 extending from valve holder 10 have cut-out portions 20 engaging the inner periphery of valve 8, legs 9 additionally being formed with openings 21 by means of which the valve 8 and valve holder 10 are joined together by sutures 22. Thus the initial unitary structure consists of valve holder 10 and valve 8 to be later disconnected as more clearly illustrated in FIG. 8. Valve 8 is provided with the usual valve cusps 23 which may be made of suitable material and in the present form may actually be the valve cusps removed from an animal such, for example, as a pig.

FIGS. 9 and 10 are similar to FIGS. 7 and 8 but illustrate the combination of a disposable valve holder 10a with an aortic valve 8a. In this form of the invention, legs 9a of valve holder 10a may be straight and form a unit with valve 8a by attachment with sutures 22a.

The manner in which the apparatus described above is utilized in an actual operation will now be described in more detail with particular reference to FIGS. 4, 5 and 6.

As shown in FIG. 4, disk 12 supporting unitary valve and valve holder 8 and 10 is being held directly above mitral annulus 2, some of the sutures 3 remaining in holder 10 while others have already been threaded through valve 8 and are supported on disk 12 by the spring clips 19. In FIG. 5, the valve is shown in place, having been pushed downwardly by rod 14 and sutures 3 attach valve 8 to annulus 2 and are all retained on clips 19 of disk 12. By loosening set screw 17 and rotating knob 18, threaded extension 15 of rod 14 is removed from the top of valve 8 and disposable valve holder 10 is discarded, leaving valve 8 in place. As shown in FIG. 6, the operation is substantially over, all sutures 3 but one having been tied and valve 8 is firmly in place, having been attached to the heart and more specifically to annulus 2.

Obviously the same procedure is used in replacing the aortic valve except that in this case valve 8a and disposable holder 10a are utilized.

FIGS. 11 and 12, illustrate a suture organizer 40 upon which are secured a number of suture holders 42 of alternative configuration. Organizer 40 is formed with a support 44 of suitable plastic such as Delrin upon which there is disposed a number of spaced holders 42, each including a pair of spaced arms 46 and 48. Arms 46, 48 are inflexible, and if formed of the same material as support 44, may be cast integral therewith. Arms 46, 48 may also be formed of other suitable material, such as stainless steel or the like, and suitably secured together as by screws, bolts or rivets. Each arm 46, 48 is cut diagonally and inwardly along its top, as shown at 50, 52 respectively to facilitate insertion of a suture between the inwardly facing wall of arms 46, 48 and an insert 60 of resilient material. Insert 60 may be formed from rubber or plastic and can be cut from either tubular material or flat stock as long as such is of proper thickness so that the tube, or flat stock when folded upon itself, will fill the space between arms 46, 48 and be compressed therebetween so that the sides of insert 60 about the inside walls of arms 46, 48, and exert a pressure thereagainst sufficient to releasably hold the sutures between insert 60 and the inside walls of arms 46, 48. If desired a pin, rivet or other suitable means 64, may be passed between arms 46, 48 and through insert 60 to secure same in place.

While the suture organizers shown in FIGS. 1 and 2, 11 and 12 are particularly useful in the replacement of heart valves and more particularly with the apparatus shown in FIGS. 4, 5 and 6, it will be apparent to those skilled in this art that they are extremely useful in supporting and separating multiple interrupted sutures in any operation where such multiple suturing is required as, for example, in the resection of the small intestine, the anterior resection of the colon, the repair of the coarctation of the aorta and the repair of indirect inguinal hernia; the utility of the invention, however, is not limited to the examples given.

With respect to the disposable prosthetic device holder and the apparatus described and illustrated for performing the operation, variations in specific details are contemplated. For example, the number of legs projecting from the body of the holder may be varied and differently positioned depending upon the shape of the prosthetic device, i.e., as for a semilunar valve.

From the above description it will thus be seen that novel and improved suture organizers, and prosthetic device holders, have been shown with attendant surgical procedures; all of which are simple, efficient and most important serve to reduce the time required for surgery in operations where time is a critical factor.

It is understood that although we have shown the preferred forms of our invention that various modifications may be made in the details thereof without departing from the spirit as comprehended by the following claims.

We claim:
1. A suture holder and organizer; comprising:
   (a) a base member;
   (b) at least one pair of spaced arms extending upwardly from said base member;
   (c) resilient means disposed in said space between said pair of said spaced arms so as to be compressed therebetween but so as to permit the releasable insertion of a suture between said resilient means a surface of one said arm proximate said resilient means, said resilient means comprising a strip having a portion disposed between said spaced arms, said spaced arms being more rigid than said strip so as to compress said strip between said spaced arms.

2. The organizer of claim 1, wherein there are a plurality of pairs of spaced arms extending upwardly from said base member with resilient means so disposed between each such pair of spaced arms.

3. The organizer of claim 2, wherein said resilient means consists of a strip of rubber like material folded upon itself and sized to fill said space between said spaced arms so as to be compressed therebetween.

4. The organizer of claim 3, wherein said spaced arms each includes a lateral extension secured to said base member and said resilient strips each include lateral extensions disposed between the associated lateral extensions of said spaced arms and which are secured in place with said lateral extensions of said spaced arms.

5. The organizer of claim 1, wherein said spaced arms are flexibly secured to said base member.

6. The organizer of claim 1, wherein said spaced arms are rigidly secured to said base member.

7. The organizer of claim 1, wherein the tops of each of said spaced arms are cut-off on a slant inwardly towards said space therebetween.

8. The organizer of claim 1, wherein said resilient means is formed from a piece of tubular material cut and otherwise sized to be compressed between said spaced arms.

9. The organizer of claim 8, wherein securing means are provided for securing said resilient means in place between said spaced arms.

10. The organizer of claim 1, wherein said base member and spaced arms are formed as a unit from plastic material.

11. The organizer of claim 10, wherein said plastic material is Delrin.

* * * * *